United States Patent
Fritz et al.

(10) Patent No.: US 9,410,865 B2
(45) Date of Patent: Aug. 9, 2016

(54) SYSTEM FOR MONITORING THE LEAK TIGHTNESS OF A TANK

(75) Inventors: Thomas Fritz, Schopfheim (DE);
Thorsten Springmann, Hausen (DE);
Dirk Misselwitz, Hamburg (DE)

(73) Assignee: ENDRESS + HAUSER MESSTECHNIK GMBH + CO. KG, Weil am Rhein (DE)

( * ) Notice: Subject to any disclaimer, the term of this patent is extended or adjusted under 35 U.S.C. 154(b) by 475 days.

(21) Appl. No.: 13/994,182

(22) PCT Filed: Dec. 8, 2011

(86) PCT No.: PCT/EP2011/072242
§ 371 (c)(1),
(2), (4) Date: Jun. 14, 2013

(87) PCT Pub. No.: WO2012/080092
PCT Pub. Date: Jun. 21, 2012

(65) Prior Publication Data
US 2013/0263666 A1 Oct. 10, 2013

(30) Foreign Application Priority Data
Dec. 15, 2010 (DE) ...................... 20 2010 016 623 U

(51) Int. Cl.
*G01M 3/24* (2006.01)
*G01M 3/00* (2006.01)
(Continued)

(52) U.S. Cl.
CPC .................. *G01M 3/00* (2013.01); *B65D 90/50* (2013.01); *G01F 23/2967* (2013.01); *G01M 3/24* (2013.01); *G01M 3/2892* (2013.01); *G01N 9/002* (2013.01); *G01N 29/036* (2013.01)

(58) Field of Classification Search
CPC ................................ G01M 3/243; G01M 3/24
USPC .......................................... 73/40.5 A, 290 V
See application file for complete search history.

(56) References Cited

U.S. PATENT DOCUMENTS

| 3,782,180 A | 1/1974 | Harris |
| 6,425,283 B1 | 7/2002 | Muller |
| 7,823,744 B2 | 11/2010 | Nagler |

FOREIGN PATENT DOCUMENTS

| DE | 10047586 A1 | 6/2002 |
| DE | 10110540 A1 | 9/2002 |
| DE | 19882359 B4 | 11/2006 |
| DE | 102008040101 A1 | 1/2010 |

OTHER PUBLICATIONS

English translation of IPR, WIPO, Geneva, Jun. 27, 2013.
Anonymous, "Vibrationsgrenzschalter fur Flussigkeiten—Liquiphant T FTL20", Feb. 21, 2012.
(Continued)

*Primary Examiner* — Hezron E Williams
*Assistant Examiner* — Rodney T Frank
(74) *Attorney, Agent, or Firm* — Bacon & Thomas, PLLC

(57) ABSTRACT

A system for monitoring the leak-tightness of a tank, which is filled with a liquid with a lower density than water. The system has a liquid drain pipe, with a container that has a bottom, which is integrated horizontally in the liquid drain pipe with a damming element, which divides the container into a partial area on the supply flow side and partial area on the drain side. A first vibronic measuring device with a first vibrating unit protruding into the supply flow side partial area of the bottom determines whether the density of the medium undershoots a specified limit. A second vibronic measuring device with a second vibrating unit, at a position not exceeding the level of the first vibrating unit, which detects whether the vibrating unit are covered with medium, and with an evaluation unit uses the measured values of measuring devices to determine whether there is liquid from the tank in the container.

8 Claims, 2 Drawing Sheets

(51) Int. Cl.
*B65D 90/50* (2006.01)
*G01F 23/296* (2006.01)
*G01M 3/28* (2006.01)
*G01N 9/00* (2006.01)
*G01N 29/036* (2006.01)

(56) References Cited

OTHER PUBLICATIONS

German Search Report, German Patent Office, Munich, Jul. 12, 2011.
International Search Report, EPO, The Netherlands, Mar. 15, 2012.

SYSTEM FOR MONITORING THE LEAK TIGHTNESS OF A TANK

TECHNICAL FIELD

This invention relates to a system for monitoring the leak-tightness of a tank, which is filled, at least partly, with a liquid, in particular, fuel, that has a lower density than water.

BACKGROUND DISCUSSION

Storage tanks, in particular for the storage of oils, for example, gasoline or other fuels, usually have a double-walled design and have a surrounding liquid collecting channel. This is connected to a drain pipe, which, for example, leads into the sewage system. Rainwater usually accumulates in the liquid collecting channel and can then flow through the drain pipe. However, if the tank has a leak, liquid in the tank can escape at this point and also accumulate in the collecting channel. Apart from the loss of the stored product, such a leak also has ecological consequences, which is why a leak detection system is used for such tanks.

Sensor cables are often used to detect a leak in the tank wall. They are installed around the bottom or around the wall and capacitively detect liquid entering the cable. The operating life and the possibility of functionally checking such sensor cables are severely restricted, however, which results in a high replacement rate. This is accompanied by high costs.

SUMMARY OF THE INVENTION

The purpose of the invention is to define a system for monitoring the leak-tightness of a tank, which has a long operating life and thus saves money in comparison with the previous solution.

The task is solved by means of a system for monitoring the leak-tightness of a tank, which is at least partly filled with a liquid, whereby the liquid has a lower density than water and which has a liquid collecting channel with a liquid drain pipe connected to it, with a container that has a bottom, which is essentially integrated horizontally in the liquid drain pipe such that the medium flowing through the liquid drain pipe accumulates in the bottom, with a damming element, which divides the container into a partial area on the supply flow side and partial area on the drain side, such that an oil separator is formed, with a first vibronic measuring device with a first vibrating unit protruding into the supply flow side partial area, which determines whether the density of the medium surrounding the first vibrating unit undershoots a specified limit, and which issues a corresponding measured value, with a second vibronic measuring device with a second vibrating unit, the highest installed position of which is level with the first vibrating unit, which detects whether the second vibrating unit is covered with medium and issues a corresponding measured value, and with an evaluation unit to which the measured values of the first measuring device and the second measuring device are supplied, and which uses the measured values to determine whether there is liquid from the tank in the container.

The two vibronic measuring devices are preferably so-called tuning forks with two paddle-shaped teeth as a unit capable of vibrating. Such devices are manufactured and marketed by the patent applicant for level and density measurement under the name 'Liquiphant'.

The system in the invention uses the drain pipeline of the collecting channel, which is already provided in regular tanks to receive oil, fuel or other hazardous substances, to install a measuring container that can already detect the leak of small quantities. The detection principle is based on the different densities of the water that is normally present in the drain system due to condensation and liquid escaping from the tank in the case of a leak.

Water accumulates at the bottom of the container installed in the drain pipe, which means that water is normally always present in the container. Both vibrating units are now covered by water so that the second measuring device normally signals 'covered' and the first measuring device measures the density of the water. A change in the density detected by the first measuring device is caused by the leakage of fuel from the tank as the escaping liquid reaches the water in the container. The damming element prevents the liquid with lower density from flowing directly from the supply side to the drain side without reaching the bottom where it is detected. Containers with a supply line, drain and a damming element for backing up the lighter liquid are used in the area of wastewater treatment plants as oil separators.

In the case of new installation of the system and, for example, due to evaporation and falling water level in the bottom, it is possible that the first vibrating unit is not or only incompletely covered with liquid. The first measuring device also signals in this case that the specified density limit value has been undershot. To avoid misinterpretation of this low density with regard to the leak-tightness of the tank, the second measuring device is installed in the container. It monitors the level of the medium at the bottom. The two vibrating units are arranged in relation to one another such that the first vibrating unit is always covered with medium when the second vibrating unit is covered. The second measuring device is therefore designed to monitor covering of the vibrating unit of the first measuring device and represents a safety function if the bottom should run dry. Only if the second measuring device indicates that the two vibrating units are covered with medium and the first measuring device signals that the density limit value has been undershot will an alarm signal be generated, which indicates the occurrence of a leak.

The first embodiment of the invention is that a controllable sealing element is installed in flow direction downstream of the partial area of the container on the drain side, which, when closed, prevents the flow of the medium from the container, and that the evaluation unit closes the sealing element if there is liquid from the tank in the container.

According to one embodiment, the second vibrating unit projects into the partial area of the bottom on the drain side.

According to one embodiment, the first and second measuring device are installed on an upper side of the container that faces the bottom and essentially project vertically into the container.

According to one embodiment, the second vibrating unit is arranged above the first vibrating unit such that covering of the first vibrating unit with medium can be monitored by the second measuring device.

According to a further embodiment of the system, at least the first vibrating unit is surrounded by a protective element that is permeable to liquid. An advantageous embodiment is that the protective element is a perforated plate.

According to one embodiment of the invention, the evaluation unit generates an alarm signal when liquid from the tank enters the container.

BRIEF DESCRIPTION OF THE DRAWINGS

The invention is explained in more detail on the basis of the following figures.

DETAILED DISCUSSION IN CONJUNCTION WITH THE DRAWINGS

Figure 1:
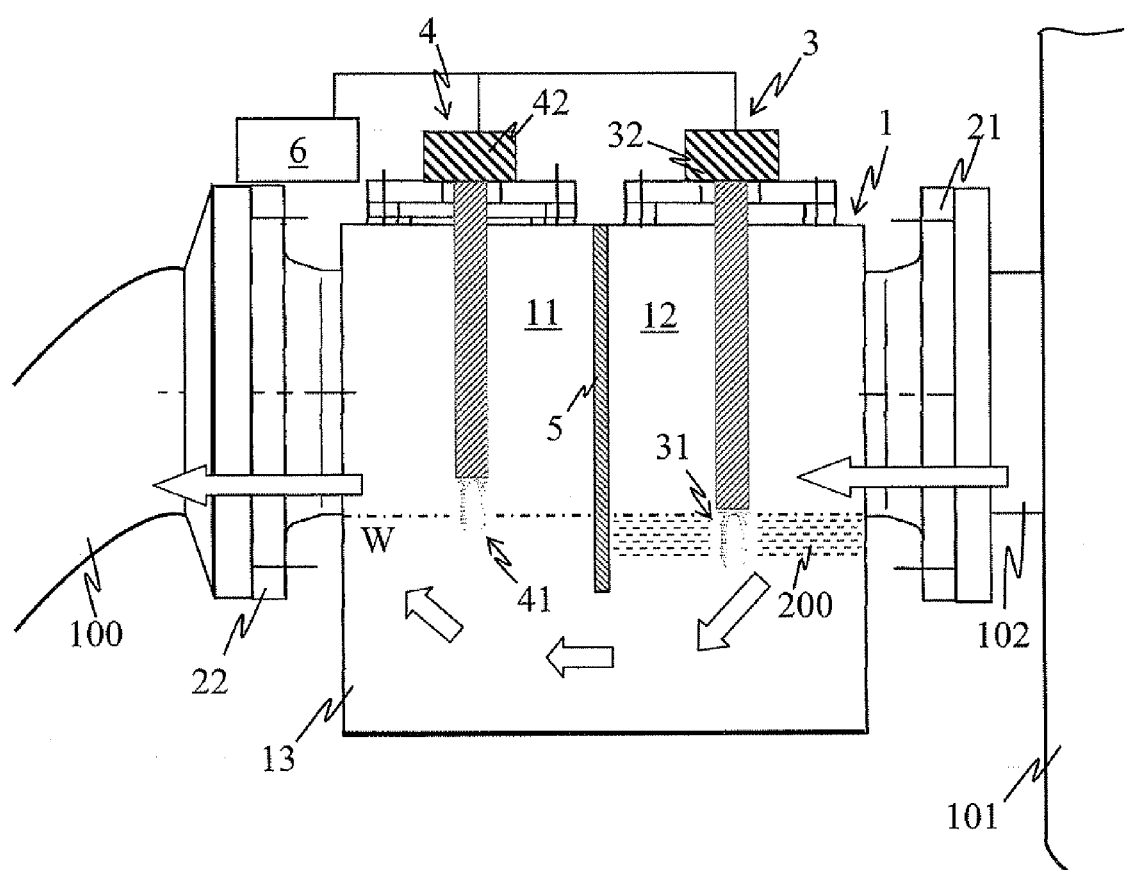
FIG. 1 shows a schematic diagram of the structure of a system for monitoring the leak-tightness of a tank.

FIG. 1 shows a schematic diagram of the structure of invented system for tank leak monitoring. The tank 101—for example, a storage tank for fuel—is only shown implicitly. The container 1 is box-shaped and has two openings arranged opposite one another with flanges 21, 22 for installation as separators in a drain pipe 100, 102, wherein the drain line 100, 102 feeds the liquid collected from a collecting channel not shown in the diagram or in the tank 101, for example, to the wastewater. In this advantageous embodiment, the container 1 is arranged between a connection piece 102 in the wall of the tank 101 and a drain pipe 100. The connection piece 102 is installed in the outer wall of the double-walled tanks 101 that are usually used for the storage of fuels or oils and are connected to the collecting channel integrated in this outer wall so that accumulated liquid is discharged via the connection piece 102. Rainwater normally flows through the drain pipe 100, 102; if there is a leak in the tank 101, the escaping stored liquid 200 is included in the flow. The openings of the container 1 preferably have the same diameter as the drain pipe 100 and the connection piece 102. However, the interior of the container 1 is designed such that a bottom 13 is formed that has to be overcome by the incoming liquid before it can flow off through the drain pipe 100. The damming element 5, which is connected at the side with the wall of the container 1, prevents a direct flow so that the incoming liquid passes the bottom 13 in every case. The arrows indicate the flow direction of the liquid.

The damming element 5 holds back the stored liquid 200 floating on the water due to the lower density when it runs into the container 1 in partial area 12 on the supply side and accumulates below the waterline W. The stored liquid 200 from the tank 101 only reaches partial area 11 of the container 1 on the drain side when the volume and pressure are sufficient to allow the liquid to flow through under the damming element 5. The invented system detects the stored liquid 200, however, even if only a small volume is present so that although the stored liquid 200 can reach partial area 11 on the drain side it can still be prevented from flowing through the drain pipe 100 due to measures implemented directly after detection.

The container 1 is installed horizontally so that the liquid collecting in the bottom 13 has a uniform fill level. The maximum level define by the height of the bottom 13 is indicated by the waterline W. A first vibronic measuring device 3 for determining the density and a second vibronic measuring device 4 for determining a limit level are installed from above in the container 1. The vibrating units 31, 41 of the vibronic measuring devices 3, 4 are secured to a pipe extension, which projects vertically into the container 1. The first measuring device 3 is located in partial area 12 of the container 1 on the supply side, whereas the second measuring device 4 is preferably installed in partial area 11 on the drain side. The first vibrating unit 31 of the first measuring device 3 is preferably arranged such that the it is located just, but completely, under the waterline W. A short distance from the base of the bottom 13 is also possible, however, the first vibrating unit 31 must be on a level that is also covered by the damming element 5. The second vibrating unit 41 of the second measuring device 4 is arranged slightly above the first vibrating unit 31. The horizontal liquid level can therefore be monitored by the second measuring device 4 to detect whether the first vibrating unit 31 is covered by liquid. The second vibrating unit 41 is positioned in relation to the first vibrating unit 31 preferably such that the switch point of the second measuring device 4, which is usually reached when the lower half of the vibrating unit 41 is covered, is accompanied by the complete covering of the first vibrating unit 31.

A housing 32, 42 for measuring devices 3, 4 in which, for example, display elements and electronics are accommodated, remains in each case outside the container 1 and is connected to an evaluation unit 6. It evaluates whether the density of liquid in partial area 12 of the container 1 on the supply side essentially corresponds to the density of water, or is lower, which means that stored liquid 200 from the tank 101 has leaked into the container 1. The evaluation unit 6 controls a sealing element, which is not shown for clarity purposes, for example, in the form of a flap or a gate valve installed downstream of partial area 11 of the container 1 on the drain side in the drain pipe 100 and, if required, prevents the flow of liquid from the container 1 into the drain pipe 100. This is required when the first measuring device 3 measures a density below a predefined limit value and, at the same time, the second measuring device 4 indicates that the second vibrating unit 41 and thus also the first vibrating unit 31 are covered with medium, i.e. are not vibrating in the air.

Figure 2:
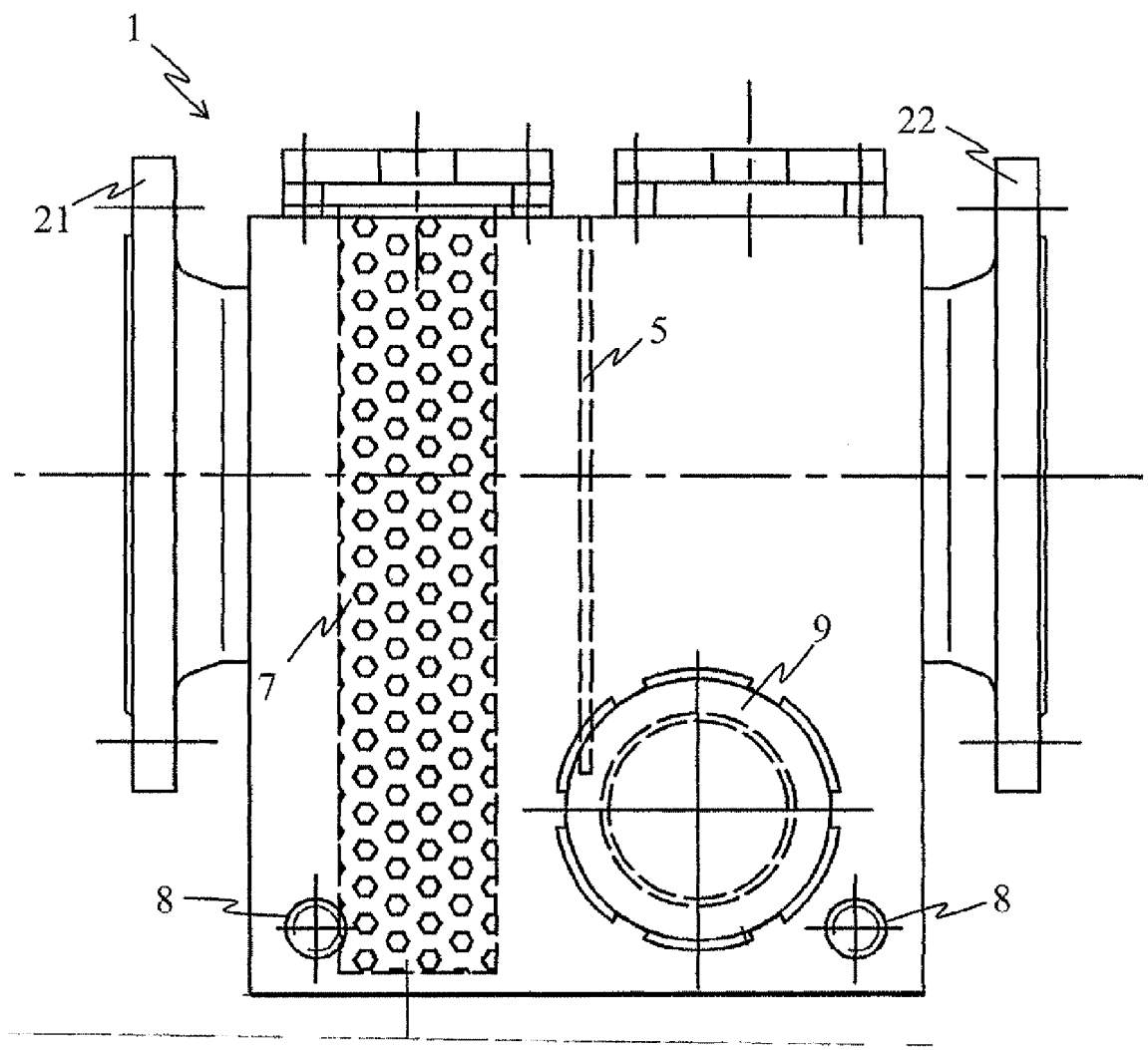
FIG. 2 shows a schematic diagram of the front view of an embodiment of the container.

FIG. 2 shows an advantageous embodiment of the container 1. A rinse connection 9 is provided in the wall of the container 1 for cleaning the vibrating elements 31, 41. For visually checking, for example, the contamination level, the liquid volume in the container 1 or the presence of liquid from the tank 101 that has entered the container 1, two inspection glasses 8 are provided in the wall. To protect the first vibrating unit 31 in the partial area 12 of the container 1, a cylinder-shaped protective element 6 is arranged around the area of the first measuring device 3 projecting into the container 1. The protective element 6 is preferably a perforated plate. This permits the unobstructed supply flow of the liquid whose density is to be determined and, at the same time, keeps large objects, for example, cleaning cloths that enter the container 1, or even animals, away from the first vibrating unit 31.

LEGEND FOR DIAGRAMS

1 Container
11 Partial area on supply side
12 Partial area on drain side
13 Bottom
21 Flange
22 Flange
3 First measuring device
31 First vibrating unit
32 Housing
4 Second measuring device
41 Second vibrating unit
42 Housing
5 Damming element
6 Evaluation unit
7 Protective element
8 Inspection glass
9 Rinse connection
100 Drain pipe
101 Tank
102 Connection piece
200 Stored liquid

The invention claimed is:
1. A system for monitoring the leak-tightness of a tank, which is filled, at least partly, with a liquid, whereby the liquid has a lower density than water, having:
 a liquid collecting channel with a liquid drain pipe connected thereto;

a container that has a bottom, which is essentially integrated horizontally in said liquid drain pipe such that the medium flowing through said liquid drain pipe accumulates in said bottom;

a damming element, which divides said container into a partial area on the supply flow side and partial area on the drain side, such that an oil separator is formed;

a first vibronic measuring device with a first vibrating unit protruding into the supply flow side partial area of said bottom, which determines whether the density of the medium surrounding said first vibrating unit undershoots a specified limit; and a second vibronic measuring device which issues a corresponding measured value with a second vibrating unit, installed at a position not exceeding the level of said first vibrating unit, and which detects whether the second vibrating unit is covered with medium and issues a corresponding measured value; and an evaluation unit to which the measured values of said first measuring device and said second measuring device are supplied, and which uses the measured values to determine whether there is liquid from the tank in said container.

2. The system as claimed in claim 1, further having:

a controllable sealing element in the flow direction downstream of the partial area of said container on the drain side, which, when closed, prevents the flow of the medium from said container, wherein:

said evaluation unit closes said sealing element if there is liquid from the tank in said container.

3. The system as claimed in claim 1, wherein:

said second vibrating element projects into the partial area of said bottom on the drain side.

4. The system as claimed in claim 1, wherein:

said first measuring device and said second measuring device are installed on an upper side of said container facing said bottom and project essentially vertically into said container.

5. The system as claimed in claim 1, wherein:

said second vibrating unit is arranged above said first vibrating unit so that covering of said first vibrating unit with medium can be monitored by said second measuring device.

6. The system as claimed in claim 1, wherein:

at least said first vibrating unit is surrounded by a liquid-permeable protective element.

7. The system as claimed in claim 6, wherein:

said protective element is a perforated plate.

8. The system as claimed in claim 1, wherein:

said evaluation unit generates an alarm signal when there is liquid from the tank in said container.

\* \* \* \* \*